(12) United States Patent
Miller (10) Patent No.: US 11,291,576 B2
(45) Date of Patent: Apr. 5, 2022

(54) DISPOSABLE STOMA PLUG AND METHOD OF USE THEREOF

(71) Applicant: Jordan Miller, Charlotte, NC (US)

(72) Inventor: Jordan Miller, Charlotte, NC (US)

( * ) Notice: Subject to any disclaimer, the term of this patent is extended or adjusted under 35 U.S.C. 154(b) by 866 days.

(21) Appl. No.: 16/104,838

(22) Filed: Aug. 17, 2018

(65) Prior Publication Data

US 2020/0054476 A1 Feb. 20, 2020

(51) Int. Cl.
*A61F 5/44* (2006.01)
*A61F 5/445* (2006.01)

(52) U.S. Cl.
CPC ............ *A61F 5/4401* (2013.01); *A61F 5/445* (2013.01); *A61F 5/4407* (2013.01); *A61F 2005/4402* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,675,642 A * | 7/1972 | Lord | ...................... | A61M 29/00 600/32 |
| 4,187,850 A * | 2/1980 | Gust | ........................ | A61F 5/445 604/338 |
| 4,209,009 A * | 6/1980 | Hennig | .................. | A61F 2/0009 604/374 |
| 4,258,704 A * | 3/1981 | Hill | ....................... | A61F 2/0009 600/32 |
| 4,344,434 A * | 8/1982 | Robertson | ............... | A61F 5/445 604/338 |
| 4,693,236 A * | 9/1987 | Leprevost | ............. | A61F 2/0018 600/32 |
| 4,850,953 A * | 7/1989 | Haber | ................... | A61F 2/0013 600/32 |
| 4,981,465 A * | 1/1991 | Ballan | ................... | A61F 2/0009 600/32 |
| 5,421,827 A * | 6/1995 | Temple | .................... | A61F 5/451 383/68 |
| 6,071,268 A * | 6/2000 | Wagner | ................... | A61F 5/445 604/338 |
| 6,409,709 B1 * | 6/2002 | Recto | ...................... | A61F 5/445 604/338 |
| 8,070,736 B2 * | 12/2011 | Nishtala | .................... | A61F 5/44 604/327 |
| 8,075,539 B2 * | 12/2011 | Nishtala | ............... | A61F 5/4405 604/326 |
| 8,343,119 B2 * | 1/2013 | Mayer | .................... | A61F 5/443 604/338 |

(Continued)

*Primary Examiner* — Guy K Townsend
(74) *Attorney, Agent, or Firm* — Jeffrey C. Watson; Grell & Watson Patent Attorneys LLC (57) ABSTRACT

A disposable stoma plug includes an absorbent body and a grip device. The absorbent body has a bottom end and a top. The bottom end is configured for insertion into a stoma opening. The grip device is connected to the top of the absorbent body. The grip device is configured for handling the absorbent body for inserting and removing the absorbent body into and from the stoma opening. Wherein, the stoma plug is configured to briefly seal off the stoma opening of an urostomy, an ileostomy, or a colostomy to prevent bodily fluids from leaking from the stoma opening, thereby, keeping surrounding skin free and dry while changing dressings, bandages or a collection bag.

10 Claims, 6 Drawing Sheets

(56) References Cited

U.S. PATENT DOCUMENTS

| | | | |
|---|---|---|---|
| 9,636,249 B2* | 5/2017 | Davies | A61F 5/445 |
| 10,130,505 B2* | 11/2018 | Guidry | A61F 5/443 |
| 10,357,394 B2* | 7/2019 | Guidry | A61F 5/4407 |
| 10,478,328 B2* | 11/2019 | Guidry | A61F 5/445 |
| 2006/0058576 A1* | 3/2006 | Davies | A61F 5/445 |
| | | | 600/32 |
| 2008/0015405 A1* | 1/2008 | Davies | A61F 5/445 |
| | | | 600/32 |
| 2009/0275795 A1* | 11/2009 | Martino | A61F 5/445 |
| | | | 600/32 |
| 2010/0145292 A1* | 6/2010 | Mayer | A61F 5/445 |
| | | | 604/337 |
| 2015/0209173 A1* | 7/2015 | Kratky | A61F 5/445 |
| | | | 604/337 |
| 2016/0067027 A1* | 3/2016 | Shalon | A61F 2/0004 |
| | | | 600/32 |
| 2017/0156917 A1* | 6/2017 | Guidry | A61F 5/4404 |
| 2018/0028347 A1* | 2/2018 | Guidry | A61F 5/445 |
| 2019/0262167 A1* | 8/2019 | Guidry | A61F 5/445 |
| | | | 604/337 |
| 2020/0054476 A1* | 2/2020 | Miller | A61F 5/4401 |
| | | | 604/337 |

* cited by examiner

DISPOSABLE STOMA PLUG AND METHOD OF USE THEREOF

FIELD OF THE DISCLOSURE

The present disclosure is directed toward surgically created artificial stomas, such as a urostomy, ileostomy, colostomy, or the like. More specifically, the instant disclosure is directed toward a disposable stoma plug for temporarily plugging a stoma opening during changing of bandages, dressings, collection bags, or the like, and methods of use thereof.

BACKGROUND

Generally speaking, a stoma, or stomata, in anatomy is any opening in the body, such as the mouth. However, any hollow organ can be manipulated into an artificial stoma as necessary, including, but not limited to, esophagus, stomach, duodenum, ileum, ureters, urinary bladder, the like, etc. Stomata are found in particular in procedures involving the gastrointestinal tract (GIT) or gastrointestinal system (GIS). The GIT begins at the mouth or oral cavity and continues until its termination, which is the anus. Many stomata are found involving the gastrointestinal and urinary tracts. The most common surgical procedures to create an ostomy for elimination include, but are not limited to: colostomies, ileostomies, and urostomies.

These surgical procedures are invoked usually as a result of and solution to disease in the GIT. The point of exiting the body is what is known as the stoma or stoma opening. For greatest success and to minimize negative effects, it is preferable to perform this procedure as low down in the tract as possible, as this allows the maximal amount of natural digestion to occur before eliminating fecal matter from the body. The stoma is usually covered with a removable pouching system (adhesive or mechanical) or collection bag that collects and contains the output for later disposal. Modern collection bag systems enable most individuals to resume normal activities and lifestyles after surgery, often with little outward physical evidence of the stoma or its pouching system.

Challenges can arise when changing the dressings, bandages, collection bags, or the like, in particular with keeping the surrounding skin dry. Because of the nature of a stoma and the need for clean openings, care givers and patients are often times faced with having to change the dressings, bandages, collection bags, or the like, whereby the stoma is exposed for brief periods of time between changes. This brief period of time can allow bodily fluids, like fecal mater or urine, to leak from the opening onto the surrounding skin. These bodily fluids can be problematic for the open wounds, reattachment of the bandages, dressings and/or collection bags, as well as making the process unpleasant for the caregiver and/or patient. As such, there is clearly a need to provide a means and/or methods for temporarily plugging the stoma opening during bandage, dressing and/or collection bag changes that keeps the bodily fluid from leaking from the opening.

The instant disclosure of a disposable stoma plug and method of use thereof is designed to address at least certain aspects to the problems discussed above.

SUMMARY

Accordingly, in one aspect, the present disclosure embraces a disposable stoma plug. The disposable stoma plug may include an absorbent body and a grip device. The absorbent body may have a bottom end and a top. The bottom end may be configured for insertion into a stoma opening. The grip device may be connected to the top of the absorbent body. The grip device may be configured for handling the absorbent body for inserting and removing the absorbent body into and from the stoma opening. Wherein, the stoma plug may be configured to briefly seal off the stoma opening of a urostomy, an ileostomy, or a colostomy to prevent bodily fluids from leaking from the stoma opening. As such, the stoma plug may be configured for keeping surrounding skin free and dry while changing dressings, bandages or a collection bag.

One feature of the instant stoma plug according to the instant disclosure may be that the stoma plug can be disposable. As such, the instant stoma plug may be intended for a single use only.

Another feature of the instant stoma plug according to the instant disclosure may be that the absorbent body can be shaped and configured for insertion into the stoma opening to avoid trauma and stretching of the stoma opening.

Another feature of the instant stoma plug according to the instant disclosure may be that the absorbent body is also shaped and configured to fit securely into the stoma opening to prevent leaks.

In select embodiments of the instant stoma plug, the absorbent body may be configured in a conical shape. The conical shape of the absorbent body may have a base and a tip. The base of the conical shape may start at the top with the grip device, where the conical shape may extend down from the base at the grip device and extend down to the tip of the conical shape. In select embodiments, the tip of the conical shape of the absorbent body may have a rounded point.

Another feature of the instant stoma plug may be that the absorbent body can be formed of a hygienically clean absorbent material. The hygienically clean absorbent material of the absorbent body may be configured to not break apart inside the stoma opening. In select embodiments, the hygienically clean absorbent material may be a hygienically clean gauze, a hygienically clean mesh material, the like, or combinations thereof. As such, the hygienically clean gauze or the hygienically clean mesh material may be formed into the conical shape.

Another feature of the instant stoma plug may be that the grip device can be formed from a non-permeable material. The non-permeable material of the grip device may be configured to cover the top of the absorbent body to prevent bodily fluids from flowing out. In select embodiments, the non-permeable material of the grip device may be a hygienically clean plastic material.

Another feature of the instant stoma plug may be that the grip device can have a diameter larger than the absorbent body. This larger diameter of the grip device may create a lip around the grip device. This lip around the grip device may be configured to prevent the grip device from entering into the stoma opening.

Another feature of the instant stoma plug may be that the grip device can have a thickness with raised portions. The thickness with the raised portions may be configured for gripping the stoma plug.

In select embodiments of the instant stoma plug, the grip device may include a bottom surface with a cutout. In addition, the top of the absorbent body may include a protrusion configured to be inserted into the cutout of the grip device. Wherein, the grip device may be connected to the top of the absorbent body by connecting the top of the absorbent body with the bottom surface of the grip device. Whereby, when connected, the protrusion on the top of the absorbent body is inserted into the cutout on the bottom surface of the grip device.

In another aspect, the instant disclosure embraces a disposable stoma plug that consists only of the absorbent body and the grip device. The absorbent body has a bottom end configured for insertion into a stoma opening and a top. The grip device is connected to the top of the absorbent body and is configured for handling the absorbent body for inserting and removing the absorbent body into and from the stoma opening. Wherein, the instant disposable stoma plug is configured to briefly seal off the stoma opening to prevent bodily fluids from leaking. As such, the instant disposable stoma plug may be configured for keeping surrounding skin free and dry while changing dressings, bandages or a collection bag.

One feature of the instant disposable stoma plug according to the instant disclosure is that the stoma plug can be disposable. As such, the instant disposable stoma plug is configured for a single use only.

Another feature of the instant disposable stoma plug according to the instant disclosure may be that the absorbent body can be shaped and configured for insertion into the stoma opening to avoid trauma and stretching of the stoma opening.

Another feature of the instant disposable stoma plug according to the instant disclosure may be that the absorbent body is also shaped and configured to fit securely into the stoma opening to prevent leaks.

In select embodiments of the instant disposable stoma plug, the absorbent body is configured in a conical shape. The conical shape of the absorbent body has a base and a tip. The base of the conical shape starts at the top with the grip device, where the conical shape extends down from the base at the grip device and extends down to the tip of the conical shape. In select embodiments, the tip of the conical shape of the absorbent body has a rounded point.

Another feature of the instant disposable stoma plug is that the absorbent body is formed of a hygienically clean absorbent material. The hygienically clean absorbent material of the absorbent body is configured to not break apart inside the stoma opening. In select embodiments, the hygienically clean absorbent material is a hygienically clean gauze, a hygienically clean mesh material, the like, or combinations thereof. As such, the hygienically clean gauze or the hygienically clean mesh materials are formed into the conical shape.

Another feature of the instant disposable stoma plug is that the grip device is formed from a non-permeable material. The non-permeable material of the grip device is configured to cover the top of the absorbent body to prevent bodily fluids from flowing out. In select embodiments, the non-permeable material of the grip device is a hygienically clean plastic material.

Another feature of the instant disposable stoma plug may be that the grip device can have a diameter larger than the absorbent body. This larger diameter of the grip device may create a lip around the grip device. This lip around the grip device may be configured to prevent the grip device from entering into the stoma opening.

Another feature of the instant disposable stoma plug is that the grip device has a thickness with raised portions. The thickness with the raised portions is configured for gripping the stoma plug.

In another aspect, the present disclosure embraces a method of temporarily plugging a stoma opening during changing of dressings, bandages and/or a collection bag. The method may generally include the step of providing the disposable stoma plug in any of the various embodiments shown and/or described herein. As such, the provided stoma plug may include an absorbent body and a grip device. The absorbent body may have a bottom end and a top. The bottom end may be configured for insertion into a stoma opening. The grip device may be connected to the top of the absorbent body. The grip device may be configured for handling the absorbent body for inserting and removing the absorbent body into and from the stoma opening. With this provided stoma plug, the method of temporarily plugging a stoma during changing of dressings, bandages and/or a collection bag may further include the steps of: removing old dressings, bandages or collection bag from the stoma opening; inserting the bottom end of the absorbent body of the provided stoma plug into the stoma opening; preparing new dressings, bandages and/or a collection bag for the stoma opening; removing the stoma plug from the stoma opening; applying the new dressings, bandages or a collection bag on the stoma opening; and discarding the stoma plug.

In select embodiments of the instant method of temporarily plugging a stoma opening during changing of dressings, bandages and/or a collection bag, the step of inserting the bottom end of the absorbent body of the provided stoma plug into the stoma opening may be done immediately after the step of removing old dressings, bandages or the collection bag from the stoma opening thereby preventing any bodily fluid from leaking on the surrounding skin.

In other select embodiments of the instant method of temporarily plugging a stoma opening during changing of dressings, bandages and/or a collection bag, the step of applying the new dressing, bandages or the collection bag for the stoma opening may be done immediately after removing the stoma plug from the stoma opening to prevent any bodily fluid from leaking on the surrounding skin.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The present disclosure will be better understood by reading the Detailed Description with reference to the accompanying drawings, which are not necessarily drawn to scale, and in which like reference numerals denote similar structure and refer to like elements throughout, and in which.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to the instant disclosure, as shown in FIGS. 1-7, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples.

Referring now specifically to FIGS. 1-6, in a possibly preferred embodiment, the present disclosure overcomes the above-mentioned disadvantages and meets the recognized need for such an apparatus or method by providing of disposable stoma plug 10, also referred to herein as just stoma plug 10. Disposable stoma plug 10 may include absorbent body 12 and grip device 20. Absorbent body 12 may have bottom end 14 and top 18. Bottom end 14 may be configured for insertion into stoma opening 16. Grip device 20 may be connected to top 18 of absorbent body 12. Grip device 20 may be configured for handling absorbent body 12 for inserting and removing absorbent body 12 into and from stoma opening 16. Wherein, disposable stoma plug 10 may be configured to briefly seal off stoma opening 16 of urostomy 22, ileostomy 24, or colostomy 26 to prevent bodily fluids 28 (including, but not limited to, fecal matter, urine, blood, the like, etc.) from leaking from stoma opening 16, thereby, keeping surrounding skin 30 free and dry while changing any dressings 32, bandages 34, collection bag 36, the like, or combinations thereof.

Figure 5:
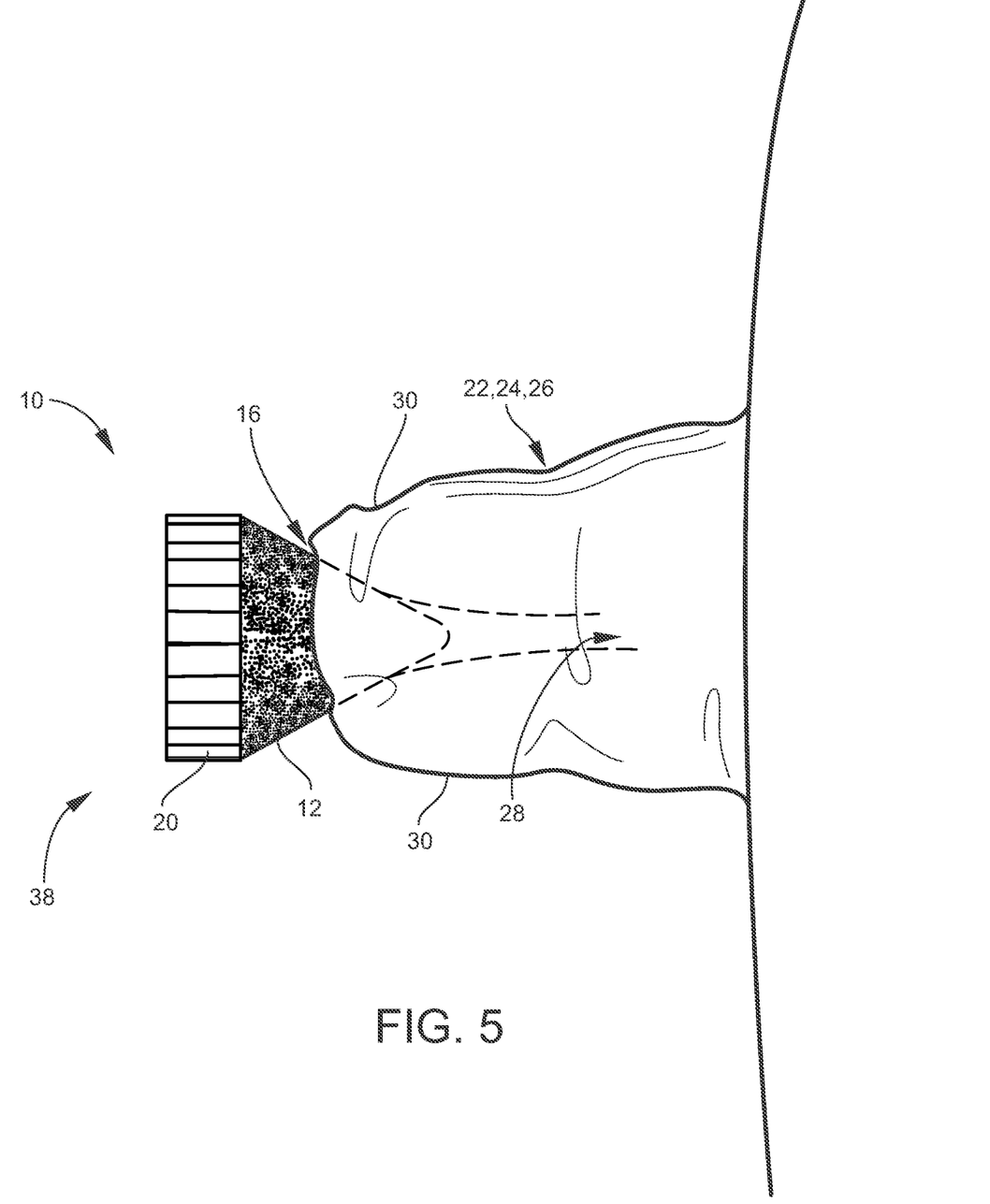
FIG. 5 is a side view of the disposable stoma plug of FIG. 1 being inserted into a stoma opening.
Figure 6:
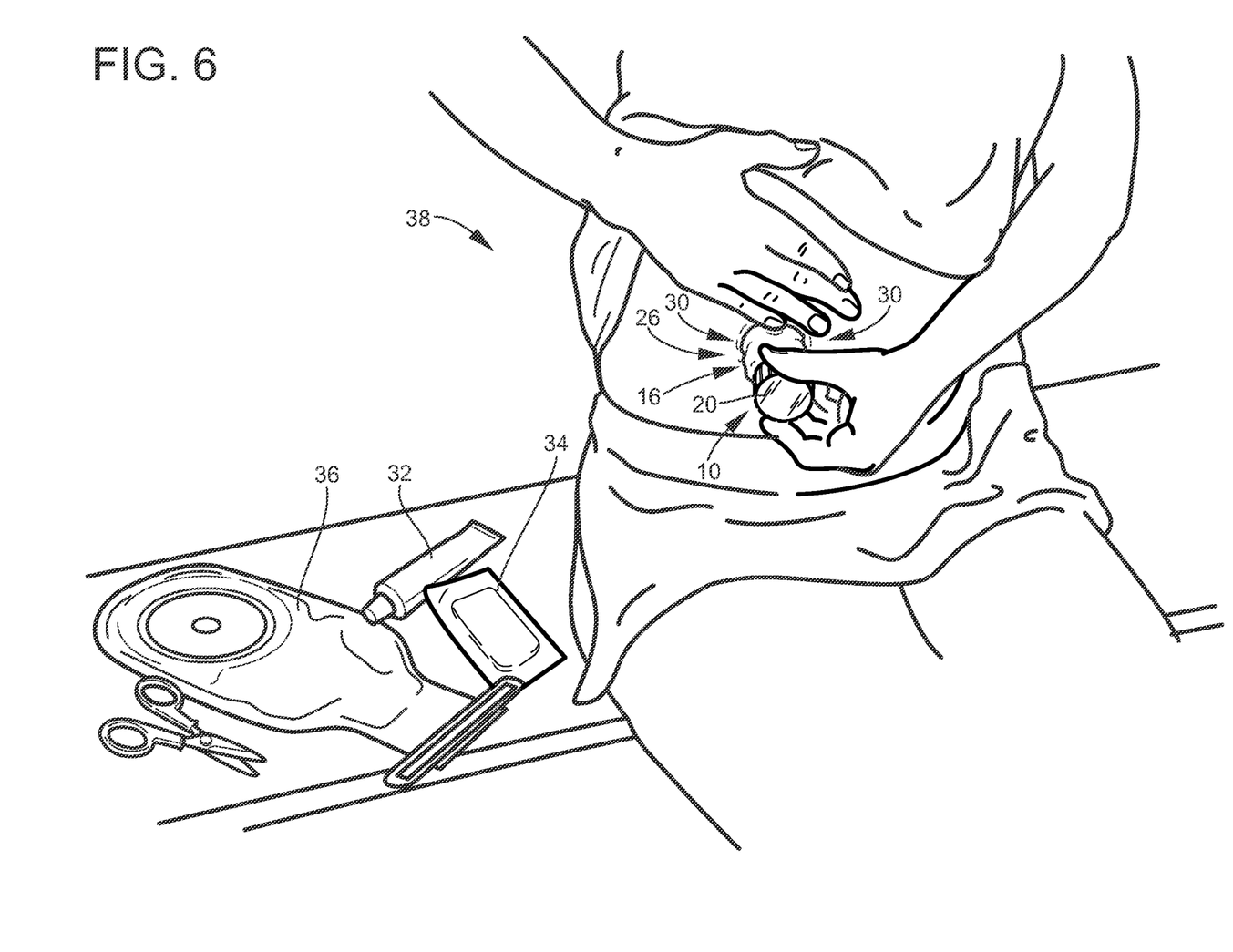
FIG. 6 is an environmental perspective view of the disposable stoma plug of FIG. 1 being temporarily inserted into the stoma for plugging the stoma during changing of dressing, bandages and/or a collection bag.

Disposable stoma plug 10 may be designed for single use 38 only, as shown in FIGS. 5 and 6. As such, disposable stoma plug 10 may be disposable.

Figure 1:
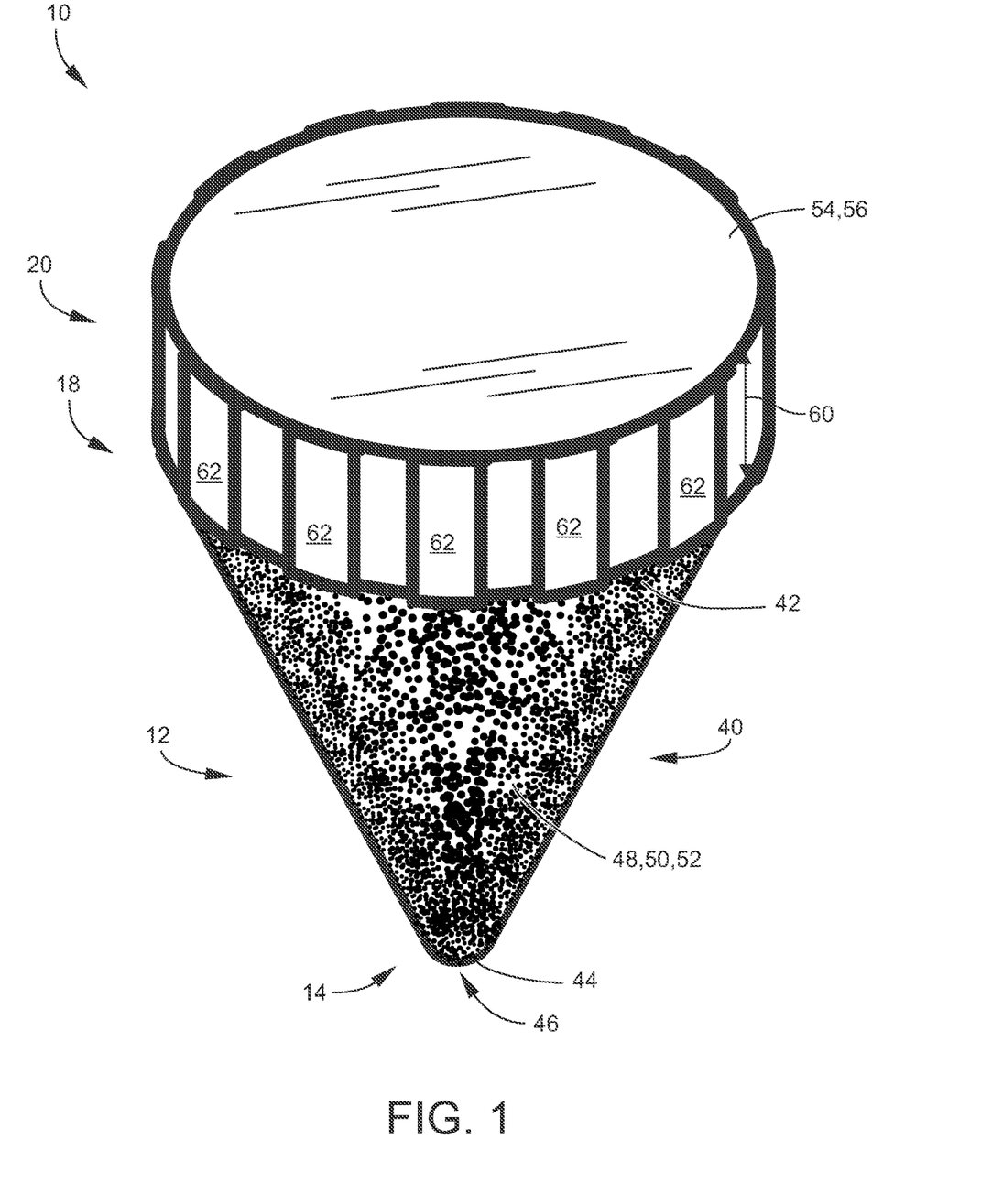
FIG. 1 is a perspective view of the disposable stoma plug according to select embodiments of the instant disclosure.
Figure 3:
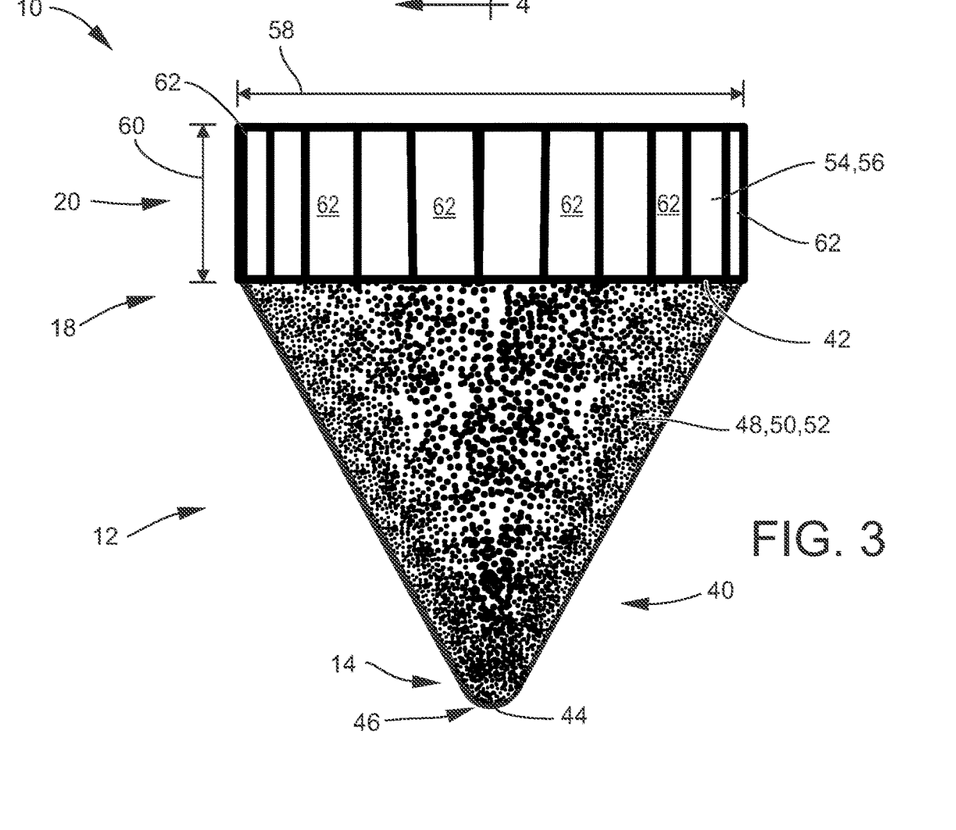
FIG. 3 is a side view of the disposable stoma plug of FIG. 1.
Figure 4:
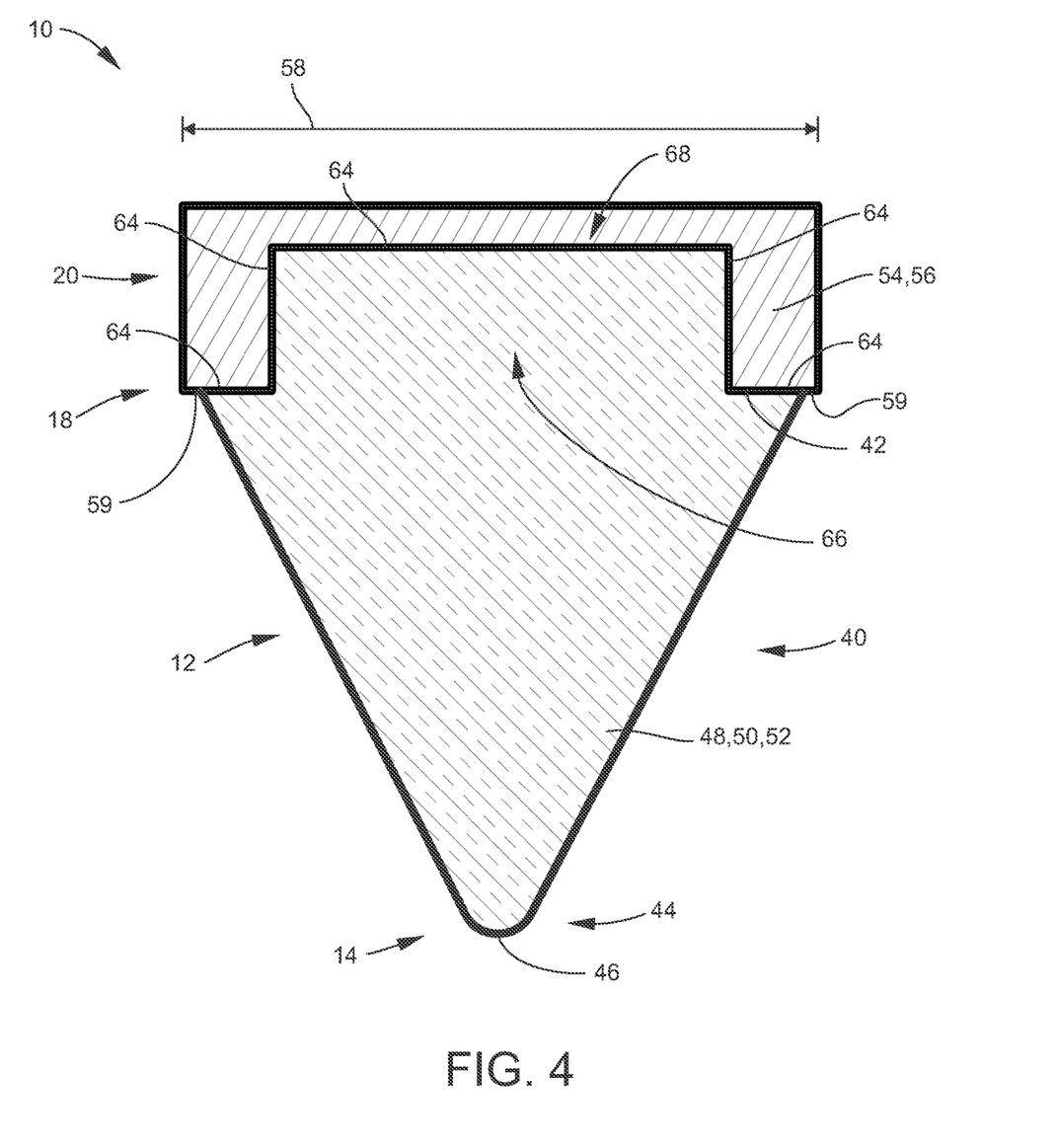
FIG. 4 is a cross-sectional view of the disposable stoma plug of FIG. 1.

Absorbent body 12 can be shaped for insertion into stoma opening 16, as shown in FIGS. 5 and 6. Absorbent body 12 can be provided in any desired style or shape for insertion into stoma opening 16. Absorbent body 12 can be configured and sized to securely fit into stoma opening 16 to prevent leaks from stoma opening 16. However, absorbent body 12 should be sized and configured not too tightly to avoid trauma and stretching of the stoma opening. In select embodiments of stoma plug 10, as shown in FIGS. 1 and 3-4, absorbent body 12 may be configured in conical shape 40. Conical shape 40 of absorbent body 12 may have base 42 and tip 44. Base 42 of conical shape 40 of absorbent body 12 may start at top 18 of absorbent body 12 with grip device 20, where conical shape 40 may extend down from base 42 at grip device 20 and extend down to tip 44 of conical shape 40. In select embodiments, tip 44 of conical shape 40 of absorbent body 12 may have rounded point 46. Rounded point 46 may provide for a rounded or dull tip for insertion into stoma opening 16.

Absorbent body 12 can be formed of any desired material or combination of materials for creating disposable stoma plug 10. In select possibly preferred embodiments, absorbent body 12 of disposable stoma plug 10 may be created from hygienically clean absorbent material 48. Hygienically clean absorbent material 48 may be for providing an absorbent material or section of disposable stoma plug 10 for absorbing bodily fluids 28 from stoma opening 16, while also being safe to use in and around stoma opening 16. As such, one feature of hygienically clean absorbent material 48 of absorbent body 12 may be that it can be configured to not break apart inside stoma opening 16. In select embodiments, hygienically clean absorbent material 48 may be, but is clearly not limited thereto, hygienically clean gauze 50, hygienically clean mesh material 52, the like, or combinations thereof. As such, hygienically clean gauze 50 or hygienically clean mesh material 52 may be formed into conical shape 40 for creating absorbent body 12 of disposable stoma plug 10.

Figure 2:
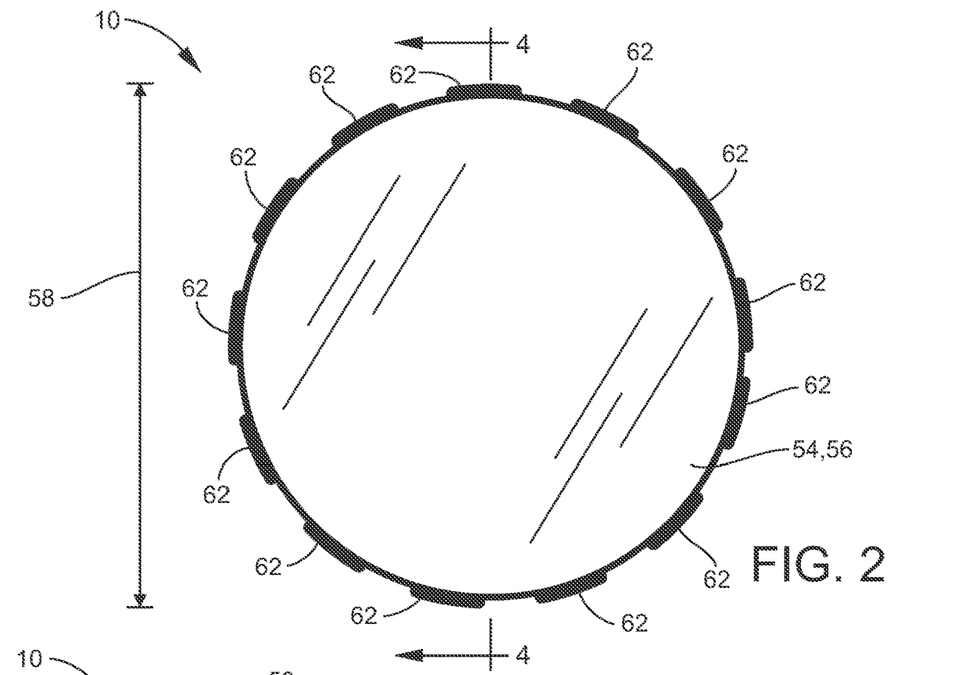
FIG. 2 is a top view of the disposable stoma plug of FIG. 1.

Grip device 20 may be included with disposable stoma plug 10. Grip device 20 can be formed from any desired material or combinations of materials for creating disposable stoma plug 10. In select possibly preferred embodiments, grip device 20 may be formed from non-permeable material 54. Non-permeable material 54 of grip device 20 may be configured to cover top 18 of absorbent body 12 to prevent bodily fluids 28 from flowing out. In select embodiments, non-permeable material 54 of grip device 20 may be hygienically clean plastic material 56, as shown in FIGS. 1-4. In select embodiments, as shown in FIGS. 1-4, grip device 20 can have diameter 58 larger or wider than absorbent body 12, including any portion of absorbent body 12. This larger diameter 58 of grip device 20 may create lip 59 around grip device 20, as best shown in FIG. 4. Diameter 58 of grip device 20 and/or lip 59 around grip device 20 may be configured to prevent grip device 20 from entering into stoma opening 16. In select embodiments, grip device 20 can have thickness 60 with raised portions 62, as shown in FIGS. 1-3. Thickness 60 with raised portions 62 may be configured for gripping stoma plug 10. Raised portions 62, as best shown in FIG. 2, may create ridges or grips throughout thickness 60 of grip device 20, similar to a standard bottle cap.

Referring now specifically to FIG. 4, in select other embodiments, grip device 20 may include bottom surface 64 with cutout 66. In addition, top 18 of absorbent body 12 may include protrusion 68 configured to be inserted into cutout 66 of grip device 20. Wherein, grip device 20 may be connected to top 18 of absorbent body 12 by connecting top 18 of absorbent body 12 with bottom surface 64 of grip device 20. Whereby, when connected, protrusion 68 on top 18 of absorbent body 12 is inserted into cutout 66 on bottom surface 64 of grip device 20. With grip device 20 having bottom surface 64 with cutout 66, grip device 20 may be configured or shaped similar to a cap or bottle cap. However, the disclosure is not so limited, and grip device 20 may be connected or attached to absorbent body 12 by any means or configuration.

As shown in FIGS. 1-4, the instant disclosure embraces a simple disposable stoma plug 10 that consists only of absorbent body 12 and grip device 20, and any means or devices configured for connecting absorbent body 12 with grip device 20 (i.e. adhesives, the like, etc.). As such, disposable stoma plug 10 consisting only of absorbent body 12 and grip device 20 may be provided as single use 38 device (as shown in FIGS. 5-6) that may be made from disposable components. With disposable stoma plug 10 provided in a manner with only two parts it should be affordable and easily accessible. In addition, this simple single use product may be made from materials that can be easily discarded.

Figure 7:
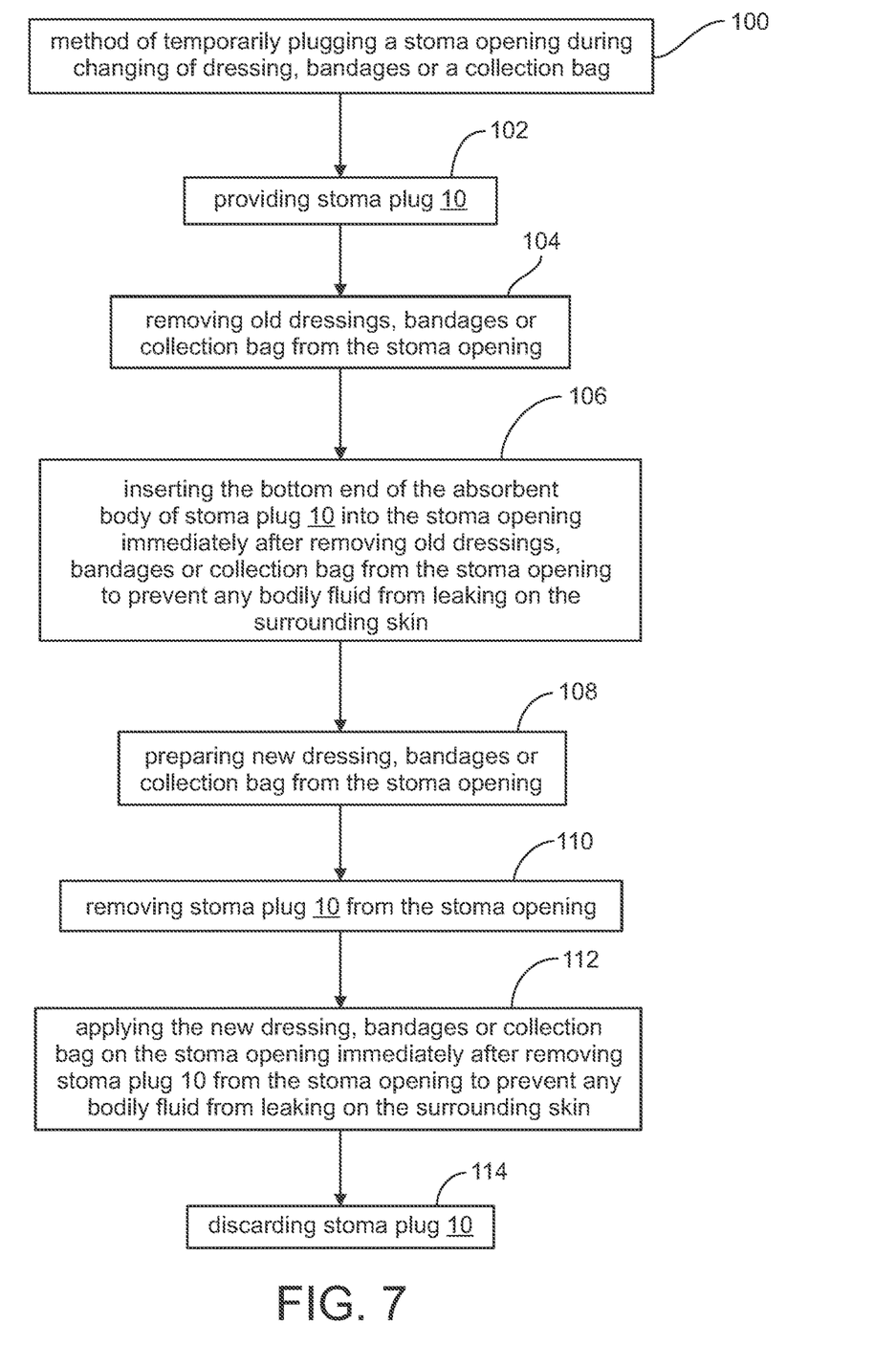
FIG. 7 is a flow chart diagram of the method of temporarily plugging a stoma during changing of dressing, bandages and/or a collection bag according to select embodiments of the instant disclosure.

Referring now to FIG. 7, in another aspect, the present disclosure embraces method 100 of temporarily plugging stoma opening 16 during changing of dressings 32, bandages 34 and/or collection bag 36 (or the like), as shown in FIG. 6. Method 100 may generally include step 102 of providing disposable stoma plug 10 in any of the various embodiments shown and/or described herein. As such, the provided stoma plug 10 may include and/or consist of absorbent body 12 and grip device 20. Absorbent body 12 may have bottom end 14 and top 18. Bottom end 14 may be configured for insertion into stoma opening 16. Grip device 20 may be connected to top 18 of absorbent body 12. Grip device 20 may be configured for handling absorbent body 12 for inserting and removing absorbent body 12 into and from stoma opening 16. With this provided stoma plug 10, method 100 of temporarily plugging stoma 16 during changing of dressings 32, bandages 34 and/or collection bag 36 (or the like) may further include the steps of: step 104 of removing old dressings 32, bandages 34 or collection bag 36 (or the like) from stoma opening 16; step 106 of inserting bottom end 14 of absorbent body 12 of the provided stoma plug 10 into stoma opening 16; step 108 of preparing new dressings 32, bandages 34 and/or collection bag 36 (or the like) for the stoma opening 16; step 110 of removing stoma plug 10 from stoma opening 16; step 112 of applying the new dressings 32, bandages 34 or collection bag 36 (or the like) on stoma opening 16; and step 114 of discarding stoma plug 10.

In select possibly preferred embodiments of method 100 of temporarily plugging stoma opening 16 during changing of dressings 32, bandages 34 and/or collection bag 36 (or the like), as shown in FIG. 7, step 106 of inserting bottom end 14 of absorbent body 12 of provided stoma plug 10 into stoma opening 16 may be done immediately after step 104 of removing old dressings 32, bandages 34 or collection bag 36 (or the like) from stoma opening 16 thereby preventing any bodily fluid 28 from leaking on surrounding skin 30.

In other select possibly preferred embodiment of method 100 of temporarily plugging stoma opening 16 during changing of dressings 32, bandages 34 and/or collection bag 36 (or the like), as shown in FIG. 7, step 112 of applying new dressings 32, bandages 34 or collection bag 36 (or the like) for stoma opening 16 may be done immediately after removing stoma plug 10 from stoma opening 16 to prevent any bodily fluid 28 from leaking on surrounding skin 30.

In sum, the present disclosure embraces a single-use disposable device 10 to briefly seal off any stoma opening 16 to prevent bodily fluids 28 from leaking from the opening 16. The device 10 keeps the surrounding skin 30 free and dry while changing dressings 32, bandages 34, collection bags 36, the like, or combinations thereof. As such, disposable stoma plug 10 may be used for plugging stoma opening 16 of urostomy 22, ileostomy 24, colostomy 26, or the like, to keep surrounding skin 30 dry during a dressing, bandage or ostomy bag change. Disposable stoma plug 10 may therefore provide a way to briefly seal off any stoma opening to prevent bodily fluids 28 from leaking from the stoma opening 16, keeping surrounding skin 30 free and dry while changing dressings/bandages/collection bags or the like. Stoma plug 10 may be designed to be disposable and thus intended for single use 38 only. Stoma plug 10 may include non-permeable element, or grip device 20, to cover top 18 of absorbent body 12 to prevent bodily fluids 28 from flowing out onto surrounding skin 30, i.e. plastic or other similar material. This top or gripping device 20 of stoma plug 10 may be provided with larger diameter 58 than absorbent body 12 portion to keep it from protruding into stoma opening 16. Gripping device 20 may also be easy to grip for smooth manipulation for insertion into stoma opening 16 and retrieval from stoma opening 16. Hygienically clean absorbent material 48, such as hygienically clean gauze 50 or hygienically clean mesh material 52, may be shaped to protrude into stoma opening 16 securely or snuggly to avoid trauma and stretching of the opening. This secure fit may also help to prevent leaks. Hygienically clean absorbent material 48 of absorbent body 12 may thus be a material that is clean and cannot break apart inside the opening.

A feature of the present disclosure of disposable stoma plug 10 may be its ability to safely and effectively cover the opening of a stoma, without adhering to the skin, for temporary procedures.

Another feature of the present disclosure of disposable stoma plug 10 may be its ability to be used by most people. They can be sold commercially in hospitals to be used by a wound care and ostomy nurses, to ease the workload of dressing changes, and by people in their home environment. This very simple product may allow a broad range of users to incorporate it into their ostomy supplies.

Another feature of the present disclosure of disposable stoma plug 10 may be its ability to produce it in a cost-effective manner with only two parts it should be affordable and easily accessible. This single use product must be made from materials that can be easily discarded.

In the specification and/or figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein but is limited only by the following claims.

The invention claimed is:

1. A stoma plug comprising:
    an absorbent body with a bottom end configured for insertion into a stoma opening and a top;
    a grip device with a bottom surface directly connected to the top of the absorbent body, the grip device is configured for handling the absorbent body for inserting and removing the absorbent body into and from the stoma opening;

the absorbent body having a conical shape with a base and a tip, the base of the conical shape starting at the top with the grip device, where the conical shape extends down from the base at the grip device and extends down to the tip of the conical shape, wherein the conical shape of the absorbent body is shaped for insertion into the stoma opening to avoid trauma and stretching of the stoma opening, where the absorbent body is also shaped and configured to fit securely into the stoma opening to prevent leaks;

the absorbent body being formed of a hygienically clean absorbent material that is configured to not break apart inside the stoma opening, wherein the hygienically clean absorbent material being a hygienically clean gauze or a hygienically clean mesh material, wherein the hygienically clean gauze or the hygienically clean mesh material is formed into the conical shape;

the grip device is formed from a non-permeable material configured to cover the top of the absorbent body to prevent bodily fluids from flowing out, wherein the non-permeable material of the grip device is a hygienically clean plastic material;

the grip device has a diameter larger than the absorbent body creating a lip around the grip device configured to prevent the grip device from entering into the stoma opening; and wherein the stoma plug being configured to briefly seal off the stoma opening of an urostomy, an ileostomy, or a colostomy to prevent bodily fluids from leaking from the stoma opening, thereby, keeping surrounding skin free and dry while changing dressings, bandages or a collection bag.

2. The stoma plug of claim 1, wherein the stoma plug is disposable and configured for a single use only.

3. The stoma plug of claim 1, wherein the tip of the conical shape of the absorbent body having a rounded point.

4. The stoma plug of claim 1, wherein the grip device has a thickness with raised portions configured for gripping the stoma plug.

5. The stoma plug of claim 1, wherein:
the grip device includes the bottom surface with a cutout; and
the top of the absorbent body including a protrusion configured to be inserted into the cutout of the grip device;
wherein, the grip device is connected to the top of the absorbent body by connecting the top of the absorbent body with the bottom surface of the grip device, whereby, when connected the protrusion on the top of the absorbent body is inserted into the cutout on the bottom surface of the grip device.

6. A disposable stoma plug consisting of:
an absorbent body with a bottom end configured for insertion into a stoma opening and a top;
a grip device with a bottom surface directly connected to the top of the absorbent body, the grip device is configured for handling the absorbent body for inserting and removing the absorbent body into and from the stoma opening;
the bottom surface of the grip device includes a cutout; and
the top of the absorbent body including a protrusion configured to be inserted into the cutout of the grip device;
wherein, the grip device is directly connected to the top of the absorbent body by connecting the top of the absorbent body with the bottom surface of the grip device, whereby, when connected the protrusion on the top of the absorbent body is inserted into the cutout on the bottom surface of the grip device.

7. The disposable stoma plug of claim 6, wherein the disposable stoma plug being configured to briefly seal off the stoma opening of an urostomy, an ileostomy, or a colostomy to prevent bodily fluids from leaking from the stoma opening, thereby, keeping surrounding skin free and dry while changing dressings, bandages or a collection bag.

8. The disposable stoma plug of claim 6, wherein the disposable stoma plug is disposable and configured for a single use only.

9. The disposable stoma plug of claim 6, wherein the absorbent body is shaped and configured for insertion into the stoma opening to avoid trauma and stretching of the stoma opening, where the absorbent body is also shaped and configured to fit securely into the stoma opening to prevent leaks.

10. The disposable stoma plug of claim 6, wherein:
the absorbent body having a conical shape with a base and a tip, the base of the conical shape starting at the top with the grip device, where the conical shape extends down from the base at the grip device and extends down to the tip of the conical shape, wherein the tip of the conical shape of the absorbent body having a rounded point;
the absorbent body is formed of a hygienically clean absorbent material that is configured to not break apart inside the stoma opening, wherein the hygienically clean absorbent material being a hygienically clean gauze or a hygienically clean mesh material, formed into the conical shape;
the grip device is formed from a non-permeable material configured to cover the top of the absorbent body to prevent bodily fluids from flowing out, the non-permeable material of the grip device is a hygienically clean plastic material;
the grip device has a diameter larger than the absorbent body creating a lip around the grip device configured to prevent the grip device from entering into the stoma opening;
the grip device has a thickness with raised portions configured for gripping the disposable stoma plug.

* * * * *